(12) United States Patent
Yun

(10) Patent No.: US 10,294,506 B2
(45) Date of Patent: May 21, 2019

(54) METHODS FOR PRODUCING BIOLOGICAL MATERIALS

(71) Applicant: Palo Alto Investors, Palo Alto, CA (US)

(72) Inventor: Anthony Joonkyoo Yun, Palo Alto, CA (US)

(73) Assignee: Palo Alto Investors, Palo Alto, CA (US)

( * ) Notice: Subject to any disclaimer, the term of this patent is extended or adjusted under 35 U.S.C. 154(b) by 0 days.

(21) Appl. No.: 15/713,259

(22) Filed: Sep. 22, 2017

(65) Prior Publication Data

US 2018/0010161 A1 Jan. 11, 2018

Related U.S. Application Data

(62) Division of application No. 13/946,759, filed on Jul. 19, 2013, now Pat. No. 9,803,227.

(60) Provisional application No. 61/674,232, filed on Jul. 20, 2012.

(51) Int. Cl.
| | |
|---|---|
| *C12P 21/00* | (2006.01) |
| *C12P 21/02* | (2006.01) |
| *C07K 14/00* | (2006.01) |
| *C07K 16/00* | (2006.01) |

(52) U.S. Cl.
CPC .............. *C12P 21/00* (2013.01); *C07K 16/00* (2013.01); *C12P 21/02* (2013.01)

(58) Field of Classification Search
CPC ........... C12P 21/00; C12P 21/02; C07K 16/00
See application file for complete search history.

(56) References Cited

U.S. PATENT DOCUMENTS 9,803,227 B2 * 10/2017 Yun ...................... C12P 21/00

OTHER PUBLICATIONS

Chung et al., "Differential Adaptive Responses to Chronic Stress of Maternally Stressed Male Mice Offspring", Endocrinology, 146(7):3202-3210, 2005.
Dorner et al., The Stress Response in Chinese Hamster Ovary Cells, 265(5), 22029-22034,1990.
Dove, Alan, "Uncorking the biomanufacturing bottleneck", nature biotechnology, 20:777-779, 2002.
Eaglestone et al., "Translation termination efficiency can be regulated in *Saccharomyces cerevisiae* by environmental stress through a prion-mediated mechanism", The EMBO Journal, 8(7),1974-1981,1999.
Ercal et al., "In Vivo Indices of Oxidative Stress in Lead-Exposed C57BL/6 Mice Are Reduced by Treatment With Meso-2,3-Dimercaptosuccinic Acid or N- Acetylcysteine", Free Radical Biology & Medicine, 21(2)157-161, 1996.
Feng et al., "Stressed apoptotic tumor cells stimulate dendritic cells and induce specific cytotoxic T cells", 100:4108-4115, 2002.
Galbraith et al., "Control of Culture Environment for Improved Polyethylenimine-MediatedTransient Production of Recombinant Monoclonal Antibodies by CHO Cells", American Chemical Society and American Institute of Chemical Engineers, A-J, 2006.
Gawrylewski, Andrea, "The Trouble with Models, Why did human trials fail", 21(7), 1-8, 2007.
Gibson, Marylou G., "Introduction to Biotechnology Manufacturing", UCSD Extension, 2005.
Jacob et al., "Using Genomic Tools to Improve the Production of Biologics", CEP, 36-42, 2009.
Kultz, Dietmar, "Molecular and Evolutionary Basis of the Cellular Stress Response", Annu. Rev. Physiol., 67:225-57, 2005.
Lacroix-Fralish et al., "Patterns of pain: Meta-analysis of microarray studies of pain" PAIN,152,1888-1898, 2011.
Langford et al., "Social Modulation of Pain as Evidence for Empathy in Mice", Science, 312:1967-70, 2006.
Lariviere et al., "Heritability of nociception. III. Genetic relationships among commonly used assays of nociception and hypersensitivity", Pain, 97:75-86, 2002.
Lynch et al., "Use with caution: Developmental systems divergence and potential pitfalls of animal models", Yale Journal of Biology and Medicine, 82:53-66, 2009.
Marques et al., "The effect of preweaning and postweaning housing on the behaviour of the laboratory mouse (*Mus musculus*)", Laboratory Animals Ltd. Laboratory Animals, 41:92-102, 2007.
Martin et al., ""Control" laboratory rodents are metabolically morbid:Why it matters", PNAS, 107(4):6127-33, 2010.
National Research Council, "Recognition and Alleviation of Distress in Laboratory Animals", Committee on Recognition and Alleviation of Distress in Laboratory Animals, National Research Council, 0-309-10818-7, 2008.
Neavs, "Animals in Research", Limitations and Dangers, http://www.neavs.org/research/limitations, 1-2, 2012.
Abilloud, et al., "The oxidative stress response: a proteomic view", CEA—Laboratoire d'Immunochimie, 1-21, 2008.
Rodriguez et al., "Enhanced Production of Monomeric Interferon-â by CHO Cells through the Control of Culture Conditions", Department of Microbiology, Biotechnol. Prog., 21:22-30, 2005.
Satori, et al., "The clinical implications of mouse models of enhanced anxiety", Future Neurol., 6(4):531-571, 2011.
Spencer et al., "Delayed behavioral effects of postnatal exposure to corticosterone in the zebra finch (*Taeniopygia guttata*)", Hormones and Behavior, 51, 273-280, 2007.
Szegezdi et al., "Mediators of endoplasmic reticulum stress-induced apoptosis", EMBO reports, 7(9):880-85, 2006.

(Continued)

*Primary Examiner* — Karen Cochrane Carlson
(74) *Attorney, Agent, or Firm* — Bret E. Field; Bozicevic, Field & Francis LLP

(57) ABSTRACT

Methods of producing biological materials from cells and organisms are provided. Aspects of the methods include modulating the stress conditions of the cells and/or organism to produce biological materials having one or more desired properties. In certain aspects, the cell or organism is evaluated to detect the presence or absence of a stressed phenotype, wherein an unstressed phenotype may be produced before the cell or organism produces the biological material of interest. The biological materials produced from such cells and organisms may be used for a variety of applications, including therapeutic, research, and other applications.

12 Claims, No Drawings

(56) References Cited

OTHER PUBLICATIONS

Weinstock, Marta, "The long-term behavioural consequences of prenatal stress", Neuroscience and Biobehavioral Reviews, 1-14, 2008.

Wennmalm et al., "Analytical strategies for identifying relevant phenotypes in microarray data", Karolinska Institutet, 1-63, 2007.

Zoon, Kathryn C., "Points to Consider in the Characterization of Cell Lines Used to Produce Biologicals", Director, Center for Biologics Evaluation and Research, 1-42, 1993.

Engber, Daniel, "The Mouse Trap", How One Rodent Rules the Lab., http://www.slate.com/articles/health_and_science/the_mouse_trap/2011/11/the_mouse_trap.html, 1-34, 2011.

Hamster Information, Hamster Care and Hamster Health, 2015, on the web at smallanimalchannel.com/hamsters/., 3 pages, accessed Feb. 26, 2015.

\* cited by examiner

METHODS FOR PRODUCING BIOLOGICAL MATERIALS

CROSS-REFERENCE TO RELATED APPLICATIONS

This application is a divisional of U.S. patent application Ser. No. 13/946,759 filed Jul. 19, 2013, and now issued as U.S. Pat. No. 9,803,227. Pursuant to 35 U.S.C. § 119 (e), this application claims priority to the filing date of U.S. Provisional Patent Application Ser. No. 61/674,232 filed Jul. 20, 2012; the disclosure of which is herein incorporated by reference.

INTRODUCTION

A variety of useful biological materials may be produced by organisms, including therapeutics (e.g. peptides and antibodies), research tools, and nutritional products. Further, certain cells that are harvested or derived from organisms may themselves be used to produce a range of useful biological materials. However, adequately maintaining and culturing the living organisms and cells to produce the desired biological materials is often a difficult problem. Current approaches may lead to the production of biological materials that have one or more problems, such as suboptimal safety, efficacy, and/or yield.

SUMMARY

Methods of producing biological materials from cells and organisms are provided. Aspects of the methods include modulating the stress conditions of the cells and/or organism to produce biological materials having one or more desired properties. In certain aspects, the cell or organism is evaluated to detect the presence or absence of a stressed phenotype, wherein an unstressed phenotype may be produced before the cell or organism produces the biological material of interest. The biological materials produced from such cells and organisms may be used for a variety of applications, including therapeutic, research, and other applications.

Methods of the present disclosure include producing a biological product from a cell, the methods involving culturing the cell containing nucleic acid encoding at least a portion of the biological product, under conditions allowing for expression of the biological product; evaluating the cell to identify the presence or absence of a stressed phenotype; and recovering the biological product.

Methods of the present disclosure also include producing a biological product from an organism, the methods involving evaluating an organism to identify the presence or absence of an unstressed phenotype; extracting a plurality of cells from the organism; introducing nucleic acid encoding at least a portion of the biological product into the plurality of cells; culturing the cells under conditions allowing for expression of the biological product; and recovering the biological product.

The methods of the present disclosure further include methods for producing a product from organism having an unstressed phenotype, the methods involving evaluating an organism to identify the presence of a stressed phenotype; producing an unstressed phenotype in the organism; maintaining the organism under conditions allowing for production of the product; and recovering the product.

The methods for determining the presence or absence of a stressed phenotype may vary, and may include visual inspection, behavioral assessment, genomic assessment, proteomic assessment, and the like. In cells or organisms identified as having a stressed phenotype, an unstressed phenotype may be produced by a variety of means, including but not limited to changing the nutritional intake (e.g., type of food, quantity of food, etc.), changing the subject's environment (e.g., temperature, exposure to light, etc.), and/or administering an agent to reduce stress. Stress reducing agents of interests include, but are not limited to, small organic compounds and peptides.

The biological products produced by the methods of the present disclosure may also vary. Biological products of interest include, but are not limited to, recombinant therapeutic proteins, viruses (e.g. recombinant viruses for gene therapy), vaccines, antibodies, proteins and peptides (e.g., enzymes, growth factors, etc.), polysaccharides, nucleic acids (including DNA and RNA), cells, and nutritional products. Methods of the present disclosure may be used in conjunction with several different production techniques known in the art, such as the production of biological products using cells in a bioreactor (e.g., mammalian, yeast, bacteria, and/or insect cells), methods involving the use of transgenic animals (e.g. goats or chickens), methods involving the use of transgenic plants (e.g., tobacco, seeds or moss), and other methods known to those of skill in the art.

In practicing the subject methods, cells of interest include, but are not limited to, CHO cells, COS cells, NS0 cells, SP2/0 cells, and YB2/0 cells. Organisms of interest include, but are not limited to: prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, and flowering plants, both monocots and dicots; and animals, including vertebrates, including fishes, birds, and mammals, e.g. rodents, primates, including humans, and the like.

DETAILED DESCRIPTION

Methods of producing biological materials from cells and organisms are provided. Aspects of the methods include modulating the stress conditions of the cells and/or organism to produce biological materials having one or more desired properties. In certain aspects, the cell or organism is evaluated to detect the presence or absence of a stressed phenotype, wherein an unstressed phenotype may be produced before the cell or organism produces the biological material of interest. The biological materials produced from such cells and organisms may be used for a variety of applications, including therapeutic, research, and other applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a biological product" includes a plurality of such biological products and reference to "the cell" includes reference to one or more cells, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the invention include methods of producing biological materials from cells and organisms, with such methods involving modulating the stress conditions of the cells and/or organism to produce biological materials having one or more desired properties.

The terms "biological material" and "biological product" may be used interchangeably herein, and refer to any product or material that is produced by a cell or organism, including the cell or organism itself. The biological material may or may not be a natural product of the cell or organism, so long as the product or material is produced by the cell or organism. Exemplary biological materials include, but are not limited to, recombinant therapeutic proteins, viruses (e.g. recombinant viruses for gene therapy), vaccines, antibodies (e.g. IgG antibodies, monoclonal antibodies, and the like), proteins and peptides (e.g., enzymes, growth factors, etc.), polysaccharides, nucleic acid including DNA and RNA, cells, and nutritional products for consumption by an organism (e.g. eggs, livestock). As used herein, a biological product that is produced by a cell or organism and subsequently modified or altered in one or more ways (e.g. glycosylation, radiolabeling, and the like) is still considered a biological product.

Thus, biological products may be viewed as those that are produced by a cell and/or organism. Organisms referred to herein may vary considerably, where the term "organism" refers to a living or once-living entity that may range in size and complexity from single cell entities to complex multicellular species. As such, organisms of interest include, but are not limited to: single celled organisms, e.g. prokaryotes, and multicellular organisms, e.g., invertebrates and vertebrates, etc. Accordingly, organisms of interest include, but are not limited to: prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as yeasts, slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, herbs, shrubs, e.g. tobacco plants, gymnosperms and flowering plants, both monocots and dicots; and animals, including sponges, members of the phylum cnidaria, e.g. jelly fish, corals and the like, comb-jellies, worms, rotifers, roundworms, annelids, molluscs, arthropods, echinoderms, acorn worms, and vertebrates, including reptiles, fishes, birds (e.g. chickens), snakes, and mammals, e.g. rodents, bovids (e.g. goats), primates, including humans, and the like. Organisms may be naturally occurring or non-naturally occurring (e.g. transgenic).

Accordingly, the "cells" referred to herein may also vary considerably, where the term "cell" refers to any cell harvested and/or derived from one or more organisms. Where an organism is a single celled organism, the terms "cell" and "organism" may thus be used interchangeably. Moreover, the term "cell" may refer to both naturally occurring and non-naturally occurring cells. Suitable cells include eukaryotic cells, such as a mammalian cell, an insect cell, a yeast cell; and prokaryotic cells, such as a bacterial cell.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula poly-* morpha, *Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the cell is *Escherichia coli*.

In the context of the current invention, a cell and/or organism is used to produce a biological material, where the material may vary greatly from therapeutic products to nutritional products. The inventors have discovered that cells and organisms used to produce biological materials may be stressed, which may lead to the production of biological materials that have one or more suboptimal properties, such as suboptimal safety, efficacy, and/or yield. Aspects of the methods include modulating the stress conditions of the cells and/or organism to produce biological materials having one or more desired properties, and/or the absence of one or more undesired properties (e.g. poor safety profile, poor efficacy, and the like).

In certain aspects, a biological product is produced by an unstressed cell or organism. The organism or cell may be acquired by any convenient means, including by purchasing from a commercial source that sells cells or organisms. Once the cell or organism has been provided, the presence or absence of a stress phenotype may be evaluated. Stress may manifest itself in a number of different phenotypic ways, ranging from outward appearance (e.g., in some way deviating from a normal, wild-type appearance) or in other ways, e.g., by changes in genomic and/or proteomic profiles. The cell and/or organism may be evaluated by one or more ways, including but not limited to: appearance to behavior to certain stressed genomic and/or proteomic profiles. A variety of different methods for evaluating stress phenotypes in cells and/or organisms are known to those of skill in the art, including those described in National Research Council. (2008) *Recognition and Alleviation of Distress in Laboratory Animals*. Washington, D.C.: The National Academies Press; Moberg G P, Mench J A (2000) *The Biology of Animal Stress. Basic Principles and implications for Animal Welfare*. Wallingford: CABI Publishing; Morton, D. B. and P. H. M. Griffiths. 1985. Guidelines on the recognition of pain, distress and discomfort in experimental animals and an hypothesis for assessment. *Vet Record* 116 (16):431-436; Kuntz, D. 2005. Molecular and evolutionary basis of the cellular stress response. *Annual Review of Physiology.* 67:225-257; Fulda, S., A. M. Gorman, O. Hari, and A. Samali. 2010. Cellular Stress Responses: Cell Survival and Cell Death. International Journal of Cell Biology. vol. 2010, Article ID 214074, 23 pages; the disclosures of which are herein incorporated by reference.

Evaluation may include visual assessment of outward phenotypic characteristics, such as visual inspection of the appearance of the cell or organism, e.g., to determine the presence of stress by identifying the presence of one or more stress correlated appearance characteristics, as described in, for example, Garner, J. P., S. M. Weisker, B. Dufour, and J. A. Mench. 2004. Barbering (fur and whisker trimming) by laboratory mice as a model of human trichotillomania and obsessive-compulsive spectrum disorder. *Comparative Med* 54 (2):216-224; the disclosure of which is herein incorporated by reference.

Evaluation may, in certain embodiments, include behavioral assessment of the cell or organism, e.g., to determine the presence of stress by identifying one or more stress correlated behavioral characteristics, such as is described in Abeyesinghe, S. M., C. M. Wathes, C. J. Nicol, and J. M. Randall. 2001. The aversion of broiler chickens to concurrent vibrational and thermal stressors. *Appl Anim Behav Sci* 73 (3):199-215; Bayne, K. A. L., S. Dexter, and S. Suomi. 1992. A preliminary survey of the incidence of abnormal behavior in rhesus monkeys (*Macaca mulatta*) relative to housing condition. *Lab Anim* 22 (5):38-44; Beck, K. D. and V. N. Luine. 2002. Sex differences in behavioral and neurochemical profiles after chronic stress: Role of housing conditions. *Physiol Behav* 75 (5):661-673; Blanchard, R. J., C. R. McKittrick, and D. C. Blanchard. 2001. Animal models of social stress: Effects on behavior and brain neurochemical systems. *Physiol Behav* 73 (3):261-271; Crawley J N. 2000. What's Wrong with My Mouse? Behavioral Phenotyping of Transgenic and Knockout Mice. New York: Wiley-Liss; Crawley J N. 2003. Behavioral phenotyping of rodents. Comp Med 53:140-146; D'Aquila, P. S., P. Brain, and P. Willner. 1994. Effects of chronic mild stress on performance in behavioural tests relevant to anxiety and depression. *Physiol Behav* 56 (5):861-867; Garner, J. P., C. L. Meehan, and J. A. Mench. 2003. Stereotypies in caged parrots, schizophrenia and autism: Evidence for a common mechanism. *Behav Brain Res* 145 (1-2):125-134; Harkin, A., T. J. Connor, J. M. O'Donnell, and J. P. Kelly. 2002. Physiological and behavioral responses to stress: What does a rat find stressful? *Lab Anim* 31 (4):42-50; Mangiavacchi, S., F. Masi, S. Scheggi, B. Leggio, M. G. De Mantis, and C. Gambarana. 2001. Long-term behavioral and neurochemical effects of chronic stress exposure in rats. *J Neurochem* 79 (6):1113-1121; Mayer, J. 2007. Use of behavior analysis to recognize pain in small animals. *Lab Anim* 36 (6):43-48; Mineur, Y. S., D. J. Prasol, C. Belzung, and W. E. Crusio. 2003. Agonistic behavior and unpredictable chronic mild stress in mice. *Behav Genet* 33 (5):513-519; Trullas, R. and P. Skolnick. 1993. Differences in fear motivated behaviors among inbred mouse strains. *Psychopharmacology* 111 (3): 323-331; Vogt, J. L., C. L. Coe, E. Lowe, and S. Levine. 1980. Behavioral and pituitary-adrenal response of adult squirrel monkeys to mother-infant separation. *Psychoneuroendocrinology* 5 (3):181-190; the disclosures of which are herein incorporated by reference.

Evaluation may, in certain embodiments, include genomic assessment of the cell or organism, e.g., to determine the presence of stress by identifying one or more stress correlated gene expression characteristics (as may be readily identified by gene expression analysis), such as is described in Cook, M. N., R. W. Williams, and L. Flaherty. 2001. Anxiety-related behaviors in the elevated zero-maze are affected by genetic factors and retinal degeneration. *Behav Neurosci* 115 (2):468-476; Mangiarini, L., K. Sathasivam, M. Seller, B. Cozens, A. Harper, C. Hetherington, M. Lawton, Y. Trottier, H. Lehrach, S. W. Davies, and G. P.

Bates. 1996. Exon 1 of the HD gene with an expanded CAG repeat is sufficient to cause a progressive neurological phenotype in transgenic mice. *Cell* 87 (3):493-506; Stenzel-Poore, M., S. C. Heinrichs, S. Rivest, G. F. Koob, and W. W. Vale. 1994. Overproduction of corticotrophin-releasing factor in transgenic mice: A genetic model of anxiogenic behavior. *J Neurosci* 14 (5 Pt 1):2579-2584; the disclosures of which are herein incorporated by reference.

Evaluation may, in certain embodiments, include proteomic assessment of the cell or organism, e.g., to determine the presence of stress by identifying one or more stress correlated protein expression characteristics (as may be readily identified using protein expression analysis), as described in Hyun, D. H., S. S. Emerson, D. G. Jo, M. P. Mattson, and R. de Cabo. 2006. Calorie restriction up-regulates the plasma membrane redox system in brain cells and suppresses oxidative stress during aging. *Proc Natl Acad Sci USA* 103 (52):19908-19912; Maier, S. F. and L. R. Watkins. 2005. Stressor controllability and learned helplessness: The roles of the dorsal raphe nucleus, serotonin, and corticotropin-releasing factor. *Neurosci Biobehav* 29 (4-5): 829-841; Muglia, L., L. Jacobson, P. Dikkes, and J. A. Majzoub. 1995. Corticotropin-releasing hormone deficiency reveals major fetal but not adult glucocorticoid need. *Nature* 373 (6513):427-432; Orr, T. E., J. L. Meyerhoff, E. H. Mougey, and B. N. Bunnell. 1990. Hyperresponsiveness of the rat neuroendocrine system due to repeated exposure to stress. *Psychoneuroendocrinology* 15 (5-6):317-328; Ulrich-Lai, Y. M. W. Xie, J. T. Meij, C. M. Dolgas, L. Yu, and J. P. Herman. 2006. Limbic and HPA axis function in an animal model of chronic neuropathic pain. *Physiol Behav* 88 (1-2):67-76; the disclosures of which are herein incorporated by reference.

Evaluation may, in certain embodiments, include the identification or quantification of a stress phenotype biomarker or physiological parameter, e.g., to determine the presence of stress by identifying one or more stress correlated biomarkers (e.g., cortisol) or physiological parameters (e.g., blood pressure), as described in Aardal, E. and A. C. Holm. 1995. Cortisol in saliva—reference ranges and relation to cortisol in serum. *Eur J Clin Chem Clin* 33 (12): 927-932; Abelson, K. S., B. Adem, F. Royo, H. E. Carlsson, and J. Hau. 2005. High plasma corticosterone levels persist during frequent automatic blood sampling in rats. In Vivo 19:815-819; Bayart, F., K. T. Hayashi, K. F. Faull, J. D. Barchas, and S. Levine. 1990. Influence of maternal proximity on behavioral and physiological responses to separation in infant rhesus monkeys (*Macaca mulatta*). *Behav Neurosci* 104 (1):98-107; Blanc, J., M. L. Grichois, and J. L. Elghozi. 1991. Effects of clonidine on blood pressure and heart rate responses to an emotional stress in the rat: A spectral study. *Clin Exp Pharmacol P* 18 (10):711-717; De Boer, S. F., S. J. Koopmans, J. L. Slangen, and G. J. van der Gugten. 1990. Plasma catecholamine, corticosterone and glucose responses to repeated stress in rats: Effect of interstressor interval length. *Physiol Behav* 47 (6):1117-1124; Dhabhar, F. S., B. S. McEwen, and R. L. Spencer. 1993. Stress response, adrenal steroid receptor levels and corticosteroid-binding globulin levels—a comparison between Sprague-Dawley, Fischer 344 and Lewis rats. *Brain Res* 616 (1-2):89-98; Klosterman, L. L, J. T. Murai, and P. K. Siiteri. 1986. Cortisol levels, binding, and properties of corticosteroid-binding globulin in the serum of primates. *Endocrinology* 118 (1):424-434; McLaren, G. W., D. W. Macdonald, C. Georgiou, F. Mathews, C. Newman, and R. Mian. 2003. Leukocyte coping capacity: A novel technique for measuring the stress response in vertebrates. *Exp Physiol* 88 (4):541-546; O'Connor, K. A., J. D. Johnson, M. K. Hansen, J. L. Wiesler-Frank, L. R. Watkins, and S. F. Maier. 2003. Peripheral and central proinflammatory cytokine response to a severe acute stressor. *Brain Res* 991:123-132; Randall, D. C., D. R. Brown, L. V. Brown, and J. M. Kilgore. 1994. Sympathetic nervous activity and arterial blood pressure control in conscious rat during rest and behavioral stress. *Am J Physiol* 267 (5 Part 2):R1241-R1249; Windle, R. J., S. A. Wood, N. Shanks, S. L. Lightman, and C. D. Ingram. 1998. Ultradian rhythm of basal corticosterone release in the female rat: Dynamic interaction with the response to acute stress. *Endocrinology* 139 (2):443-450; the disclosures of which are herein incorporated by reference.

In certain embodiments, the evaluation includes comparison to a control or reference cell or organism of a like kind that is known not be stressed, such as is described in Faraday, M. M., K. H. Blakeman, and N. E. Grunberg. 2005. Strain and sex alter effects of stress and nicotine on feeding, body weight, and HPA axis hormones. *Pharmacol Biochem Be* 80 (4):577-589; van Bogaert, M. J., L. Groenink, R. S. Oosting, K. G. Westphal, J. van der Gugten, and B. Olivier. 2006. Mouse strain differences in autonomic responses to stress. *Genes Brain Behav* 5 (2):139-149; the disclosures of which are herein incorporated by reference.

The stress condition of the cell or organism may be modulated prior to production of the biological material. For example, an unstressed phenotype may be produced in a cell or organism determined to exhibit a stressed phenotype prior to production of the biological material. An unstressed phenotype may be produced in the cell or organism using any convenient protocol, where the protocol employed may include modifying the environment of the cell or organism in some manner sufficient to produce an unstressed phenotype. Protocols of interest include those described in the references incorporated herein, including National Research Council. (2008) *Recognition and Alleviation of Distress in Laboratory Animals*. Washington, D.C.: The National Academies Press; Moberg G P, Mench J A (2000) *The Biology of Animal Stress. Basic Principles and Implications for Animal Welfare*. Wallingford: CAD Publishing; and Morton, D. B. and P. H. M. Griffiths. 1985. Guidelines on the recognition of pain, distress and discomfort in experimental animals and an hypothesis for assessment. *Vet Record* 116 (16):431-436, The term "environment" refers broadly to the overall set of conditions in which the cell or organism is present, including temperature, light, energy source availability, etc. As such, environmental modulation can be accomplished in a variety of different ways, including but not limited to: changing the temperature of the cell or organism, changing the light experienced by the cell or organism, changing the food intake of the cell or organism, administering a stress relieving agent to the cell or organism, etc. In certain embodiments, the unstressed cell or organism is produced by changing the nutritional intake of the cell or organism e.g., by modifying food intake of the cell or organism, such as by restricting or increasing the caloric intake of the cell or organism, by administering a certain kind of stress reducing food to the cell or organism (e.g., an antixenohormetic agent or organism), etc. In certain embodiments, producing an unstressed phenotype in the cell or organism includes confirming that the cell or organism has obtained the unstressed phenotype of interest, e.g., by comparing the cell or organism to a control or reference. As reviewed above, the unstressed phenotype that is produced may vary greatly, e.g., from appearance to behavior to certain unstressed genomic and/or proteomic profiles.

Because cells may be derived or harvested from an organism, in certain aspects the organism itself is first evaluated for the presence or absence of a stressed phenotype. As described above, an organism may be acquired by any convenient means, including by purchasing from a commercial source that sells organisms. Prior to harvesting or deriving the cells, the organism can be evaluated for the presence or absence of a stressed phenotype, using the approaches as reviewed above. If a stressed phenotype is identified, an unstressed phenotype may be produced, e.g. using the approaches outlined above, prior to harvesting or deriving the cells from the organism. The cells may then be used to produce a biological product. In certain aspects, the cells may also be evaluated to determine the presence or absence of a stressed phenotype, and an unstressed phenotype may be produced if a stressed phenotype is detected, following the guidance and methods reviewed above.

The evaluation of the cells or organism to determine the presence or absence of a stressed phenotype may occur prior to, during, and/or subsequent to the production of the biological material. For example, the evaluation may occur immediately prior to production of the material or at some time prior to production, e.g., about 1 month or less prior to production, 1 week or less prior to production, about 1 day or less prior to production, about 12 hours or less prior to production, about 6 hours or less prior to production, about 1 hour or less prior to production, about 30 minutes or less prior to production, about 10 minutes or less prior to production, about 5 minutes or less prior to production, etc. The evaluation may occur subsequent to the start of production, e.g. about 5 minutes or longer after the start of production, about 10 minutes or longer after the start of production, about 30 minutes or longer after the start of production, about 1 hour or longer after the start of production, about 6 hours or longer after the start of production, about 12 hours or longer after the start of production, about 1 day or longer after the start of production, about 1 week or longer after the start of production, etc. Evaluation may include a single assessment or multiple assessments of the cell or organism, specifically including assessments given before, during, and/or after production.

The methods of producing biological materials from the cells and/or organisms may be made will vary based upon, for example, the nature of the cell or organism, the nature of the biological material, the presence or absence of a stressed phenotype, and other factors readily ascertainable to those of skill in the art. In many aspects, methods of producing a biological material involve culturing a cell containing cell containing nucleic acid encoding at least a portion of the biological product, under conditions allowing for expression of the biological product; and recovering the biological product. The nucleic acid may be endogenous, or may be exogenous and be introduced into the cell or organism using methods known to those of skill in the art.

For example, standard recombinant methods can often be used for production of a biological product, such as an antibody. For instance, nucleic acids encoding light and heavy chain variable regions of the antibody, optionally linked to constant regions, may be inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Moreover, suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacterial.*, 1991: 173 (1): 86-93; Alpuche-Aranda et al., PNAS, 1992; 89 (21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbial.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

Embodiments of the invention also include methods of screening a candidate compound for its ability to modulate the stress condition of a cell or organism. By "screening" is meant assessing or evaluating an agent for its ability to modulate (i.e., change) a stress phenotype in a cell or organism that may be used to produce a biological material. As such, methods include identifying whether an agent enhances or reduces, including inhibits, a stress phenotype in a cell or organism. In practicing these embodiments of the invention, the methods may include contacting a candidate compound with an organism exhibiting a known stress phenotype (such as an organism identified as described above); and evaluating the organism to determine any change in the stress phenotype to identify the compound for its ability to modulate a stress phenotype.

The candidate agent may be contacted with the cell or organism using any convenient protocol, e.g., by placing the agent in the nutrient medium of the cell or organism, by administering the agent to the cell or organism, etc. A large number of different types of compounds may be evaluated for their ability to modulate a stress phenotype. Compounds that may be evaluated encompass numerous chemical classes, though typically they are organic molecules, preferably small organic compounds having a molecular weight of more than 50 and less than about 2,500 daltons. Compounds may include functional groups necessary for structural interaction with proteins, particularly hydrogen bonding, and may include at least an amine, carbonyl, hydroxyl or carboxyl group, such as at least two of the functional chemical groups. The compounds may include cyclical carbon or heterocyclic structures and/or aromatic or polyaromatic structures substituted with one or more of the above functional groups. Compounds of interest are also found among biomolecules including, but not limited to: peptides, saccharides, fatty acids, steroids, purines, pyrimidines, derivatives, structural analogs or combinations thereof.

Compounds of interest may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential agents may also be created using methods such as rational drug design or computer modeling.

Following contact of the compound composition with the cell or organism, the effect of the compound on the cell or organism is determined. The effect of the compound on the organism may be determined by evaluating one or more of a number of different phenotypic parameters. Phenotypic parameters that are evaluated in a given assay of the subject invention may vary widely depending, at least in part, on the nature of the cell or organism being evaluated. Phenotypic parameters that may be evaluated in any given assay include one or more of the following: (1) viability; (2) morphological defects; and (3) fecundity. Specific parameters that may be evaluated include one or more of: (1) lethal dose, e.g. LD50, LD10 etc.); (2) growth defects; (3) sterility effect dose; (4) developmental defects; (5) neurologic impairment; (6) life-span modulation, e.g. life span enhancing or shortening; and the like. Of particular interest in certain embodiments is the assessment of whether the cell or organism has reverted to a non-stressed state.

In addition to the above parameters that can be evaluated in the subject methods, the gene expression levels of the test cell or organism can be assayed, e.g. gene expression levels in treated larva, pupa, and/or flies can be evaluated. The genes can be from "houskeeping" genes that provide basic metabolic information to developmental and tissue specific genes to gauge which tissue or cell type is affected and when. A variety of different gene expression protocols, including arrays based protocols, are known to those of skill in the art, including those described in: EP 0 328 829 B1 and U.S. Pat. Nos. 5,468,613; 5,580,726; 5,599,672; 5,512,462; 5,162,209 and 5,162,209, the disclosures of which are herein incorporated by reference. Methods of analyzing differential gene expression are also described in Maniatis, et al., Molecular Cloning, A Laboratory Manual, (Cold Spring Harbor Press, Cold Spring Harbor, N.Y.) (1989); Nucleic Acid Hybridization, A Practical Approach (Hames, B. D., and Higgins, S. J. eds, IRL Press, Oxford) (1985); WO 95/21944; Chalifour, et al., Anal. Biochem. (1994) 216: 299 304; Nguyen et al., Genomics (1995) 29: 207 216; Pietu et al., Genome Res. (1996) 6: 492 503; and Zhao et al., Gene (1995) 166: 207 213.

Patents and patent applications describing methods of genomic expression analysis include, but are not limited to: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992. Also of interest are U.S. Pat. Nos. 6,656,740; 6,613,893; 6,599,693; 6,589,739; 6,587,579; 6,420,180; 6,387,636; 6,309,875; 6,232,072; 6,221,653; and 6,180,351.

Also of interest are proteomic analysis assays, e.g., where arrays of polypeptide binding agents are employed. Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

The effect of the compound on the particular physical parameter or parameters being evaluated may be determined manually or robotically, such that in many embodiments determination of the effect of the compound on the cell or organism is accomplished via an automated procedure.

The effect of the compound on the phenotypic parameter or parameters is then related to the ability of the compound to modulate the stress condition of the cell or organism.

Also provided are methods of using cells or organisms known to have unstressed phenotypes to produce a product. By known unstressed phenotype is meant that the stress state of the cell or organism is predetermined. As such, in some way the stress condition of the cell or organism has been evaluated and is known to be unstressed.

EXPERIMENTAL

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1: Production of a Biological Product from Cells

Vectors encoding a known antibody are incorporated into CHO host cells. At various timepoints, the CHO host cells are assayed to detect the presence or absence of a stressed phenotype. The cells are then divided into two groups, a control group and an experimental group. The environment of the cells of the experimental group is modulated by altering the temperature and nutritional intake of the cells. All cells—those of both the control group and the experimental group—are maintained under conditions suitable for high level expression of the nucleotide sequences. Antibodies are subsequently collected and purified. The yield and efficacy of the antibodies is assayed.

Example 2: Production of a Biological Product from an Organism

Transgenic goats that produce an antibody are divided into multiple groups. At various, the goats are assayed to detect the presence or absence of a stressed phenotype. The goats are administered different diets for four weeks. Antibodies produced during this time are assayed for efficacy, and yields are calculated. This enables identification of specific stress modulating conditions that produce antibodies that have the desired safety, efficacy, and/or yield.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for producing a biological product, the method comprising:
    evaluating a multicellular organism to identify the presence or absence of an unstressed phenotype;
    extracting a plurality of cells from the organism;
    introducing nucleic acid encoding at least a portion of the biological product into the plurality of cells;
    culturing the cells under conditions allowing for expression of the biological product; and
    recovering the biological product,
    wherein the biological product produced in a cell derived from an organism having an unstressed phenotype is different from the biological product in a cell derived from an organism not having a stressed phenotype.

2. The method according to claim 1, comprising producing the unstressed phenotype in the organism.

3. The method according to claim 2, wherein the unstressed phenotype is produced by changing the organism's nutritional intake, changing the organism's environment or both.

4. The method according to claim 3, wherein producing the unstressed phenotype comprises changing the organism's temperature or the organism's exposure to light.

5. The method according to claim 1, comprising administering to the organism an agent to reduce stress.

6. The method according to claim 5, wherein the agent is a small organic compound or a peptide.

7. The method according to claim 1, wherein evaluating the organism comprises visually inspecting the organism, behavioral assessment of the organism, genomic assessment of the organism, proteomic assessment of the organism, or a combination thereof.

8. The method according to claim 1, comprising evaluating the plurality of cells to identify the presence or absence of an unstressed phenotype.

9. The method according to claim 1, wherein the organism is a mammal.

10. The method according to claim 1, wherein the biological product is an antibody.

11. The method according to claim 10, wherein the antibody is an IgG antibody.

12. The method according to claim 1, wherein the biological product is a peptide.

* * * * *